US007472441B1

(12) United States Patent
Steffensmeier

(10) Patent No.: US 7,472,441 B1
(45) Date of Patent: Jan. 6, 2009

(54) AUTOMATIC TILT-ELEVATING CHIROPRACTIC TABLE

(75) Inventor: Lloyd A. Steffensmeier, Lisbon, IA (US)

(73) Assignee: Lloyd Table Company, Lisbon, IA (US)

( * ) Notice: Subject to any disclaimer, the term of this patent is extended or adjusted under 35 U.S.C. 154(b) by 263 days.

(21) Appl. No.: 11/458,893

(22) Filed: Jul. 20, 2006

Related U.S. Application Data

(60) Provisional application No. 60/595,626, filed on Jul. 21, 2005.

(51) Int. Cl.

| | |
|---|---|
| ***A61G 7/005*** | (2006.01) |
| ***A61G 7/05*** | (2006.01) |
| ***A61F 5/00*** | (2006.01) |

(52) U.S. Cl. ................................ 5/610; 5/611; 606/244

(58) Field of Classification Search ..................... 5/610, 5/611, 600, 614; 606/244

See application file for complete search history.

(56) References Cited

U.S. PATENT DOCUMENTS 2,630,800 A * 3/1953 Voss et al. .................. 606/244
4,059,255 A * 11/1977 Perold ........................... 5/610
5,782,870 A * 7/1998 McAfee ...................... 606/244

* cited by examiner

*Primary Examiner*—Alexander Grosz
(74) *Attorney, Agent, or Firm*—James C. Nemmers

(57) ABSTRACT

A chiropractic table has a power-operated linkage that will simultaneously tilt the table as it is lowered from an elevated position and also return the table to a horizontal position as it is elevated. The table employs a modified, movable parallelogram type of linkage, as opposed to a scissors-type linkage, which when combined with an open center frame allows the table to be lowered to a height not attainable with the prior art tables. A patient footplate assembly includes additional linkage and is operated by the tilt actuator so that when the table is elevated, the footplate is rotated out of the way, and when the table is tilted and lowered, the footplate will be rotated upwardly into position so that the patient can easily step off the table.

5 Claims, 4 Drawing Sheets

AUTOMATIC TILT-ELEVATING CHIROPRACTIC TABLE

BACKGROUND OF THE INVENTION

There are known and commercially available to the practicing chiropractor and other health care professionals and practitioners numerous types of tables to assist the practitioner in conducting examinations, adjustments and treatments beneficial to the patient. Most tables are designed so that they can be raised and lowered to a position comfortable for the practitioner to treat the patient. In addition, some tables can be tilted from a horizontal position to a near vertical position to make it easier for the patient to be positioned on the table. In such tables, there is typically provided a plate for the patient to stand on facing the table when the table is in a tilted position. This plate is commonly called the "footplate" and is not be confused with the ankle rest sometimes called a footrest. With the table in a somewhat vertical position and using the footplate, the patient can then comfortably grasp the table, whether lying facedown, face up or on either side, after which the practitioner rotates the table to a horizontal position and raises it to a desired level. Prior art tables that utilize a footplate either left the footplate in place when the table is tilted and elevated, or, if the footplate is attached to the upper part of the table, the footplate moves upwardly as the table is tilted and elevated. In the latter situation, the footplate may interfere with the treatment being provided to the patient. Also, in tables that are currently known, tilting of the table and then elevating it requires the health professional to first tilt the table and then elevate it to the desired height. This requires additional components and may add to the cost of the table. Also, additional components take up space so that the height to which the table can be lowered is limited. In certain procedures, it is desirable to have the table as low as possible, particularly if the practitioner is a short person.

It is therefore an object of the invention to provide an improved chiropractic table in which the table will automatically elevate to a desired position simultaneously with the tilting of the table thus making it easier and quicker for the health care professional to position the table to the desired height. When tilting the table is not a part of the horizontal moving mechanism, this allows the table to reach a greater range of elevation positions than otherwise available.

It is further the objection of the invention to provide an improved chiropractic table in which the footplate will automatically be rotated out of the way when the table is elevated in horizontal positions while automatically returning to the proper position for the patient to easily step off of the table.

SUMMARY OF THE INVENTION

The chiropractic table of the invention utilizes a moving, parallelogram type linkage combined with cylinders or actuators that are synchronized so as to simultaneously tilt the table upwardly as it is lowered from an elevated, horizontal position and also return the titling portion of the table to a horizontal position as it is elevated horizontally. The use of this type of linkage, offset from center, as opposed to a scissors-type linkage opens up the area in the center of the base frame and thus allows the table to be lowered and elevated to heights not attainable with the prior art tables. The patient footplate assembly includes additional linkage combined with and operated by the tilt actuator through a roller mechanism so that when the table is tilted down toward horizontal the actuator and roller combine to rotate the footplate upwardly into a rotating position to provide constant support to the patient's feet. Moreover, as the table reaches its tilted-down position, the footplate is rotated out of the way. When the table is tilted up to its vertical position, the footplate rotates into position to meet the patient's feet, providing constant support until the table has reached its tilted-up position, thus making it easy for the patient to step off the table.

DESCRIPTION OF THE PREFERRED EMBODIMENT OF THE INVENTION

Figure 1:
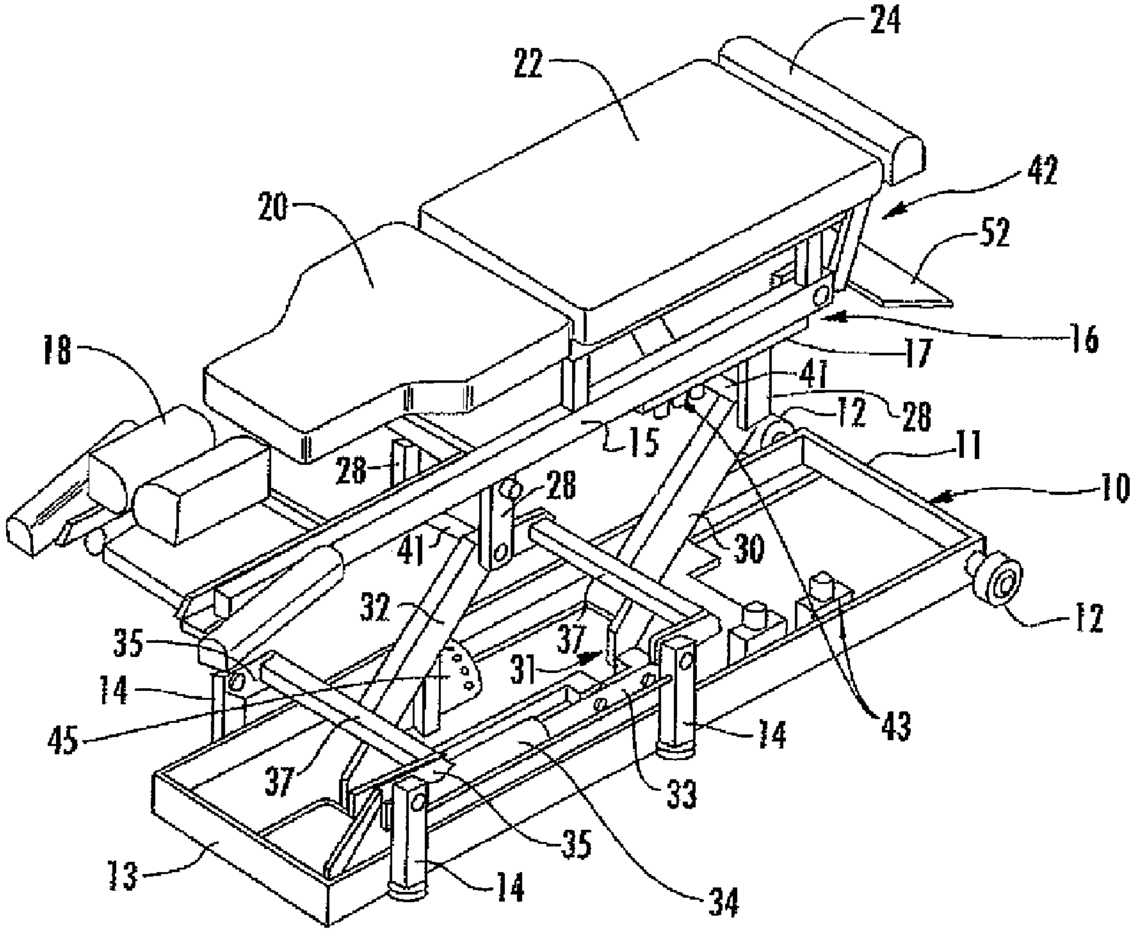
FIG. 1 is a perspective view of a table constructed according to the principles of the invention.
Figure 2:
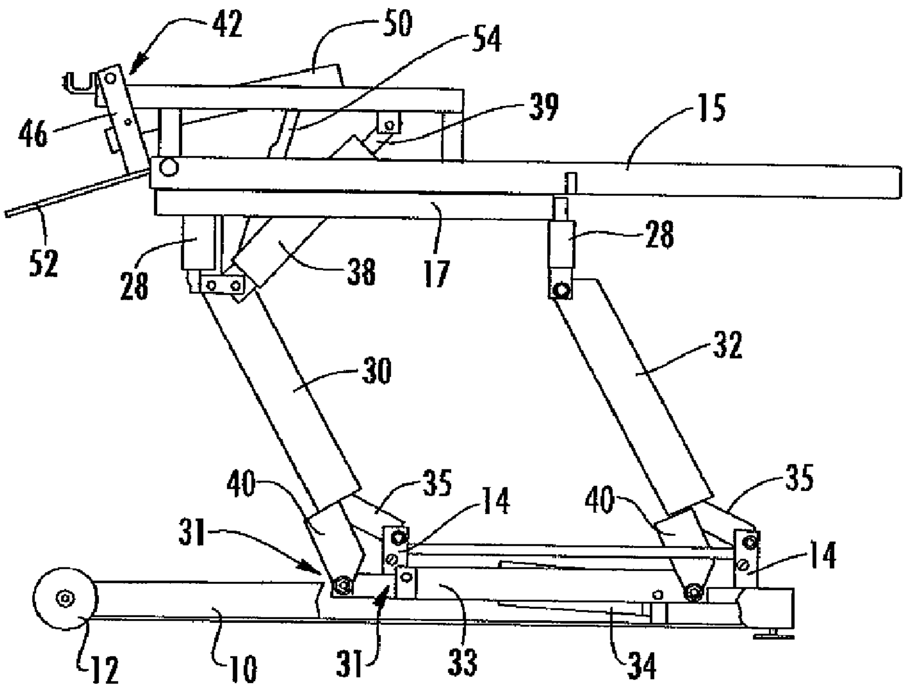
FIG. 2 is a side elevational view of the table with the cushions removed and showing the table in a raised horizontal position.
Figure 3:
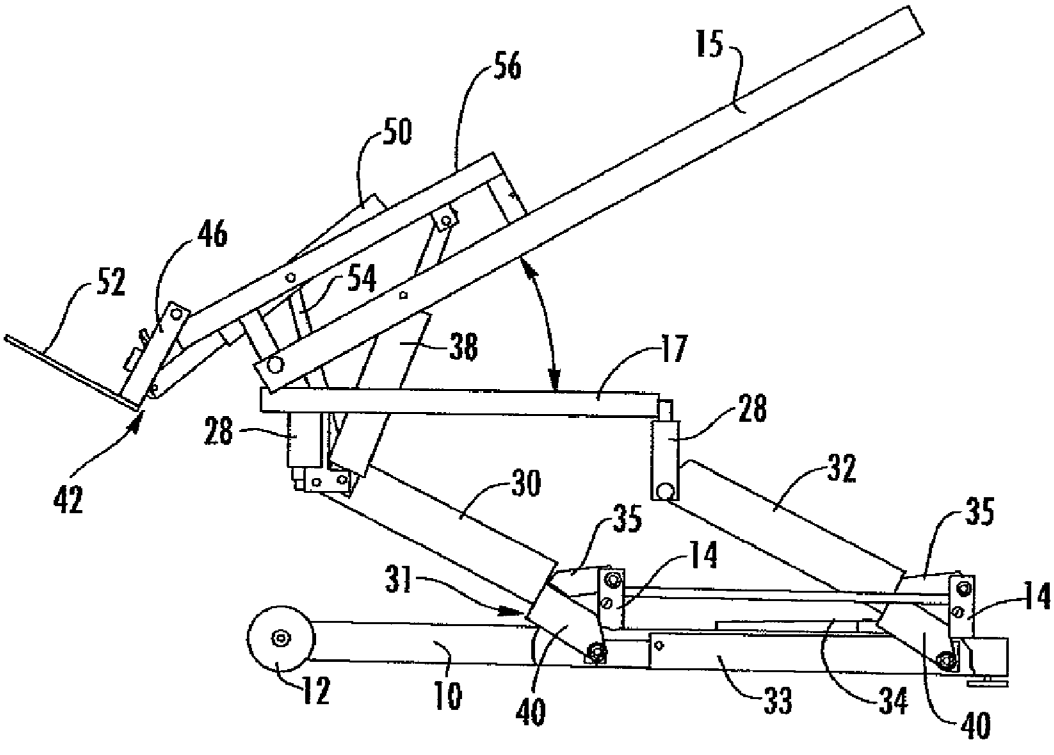
FIG. 3 is a side elevational view similar to FIG. 2 but showing the table as it descends horizontally and the frame tilts upwardly.
Figure 4:
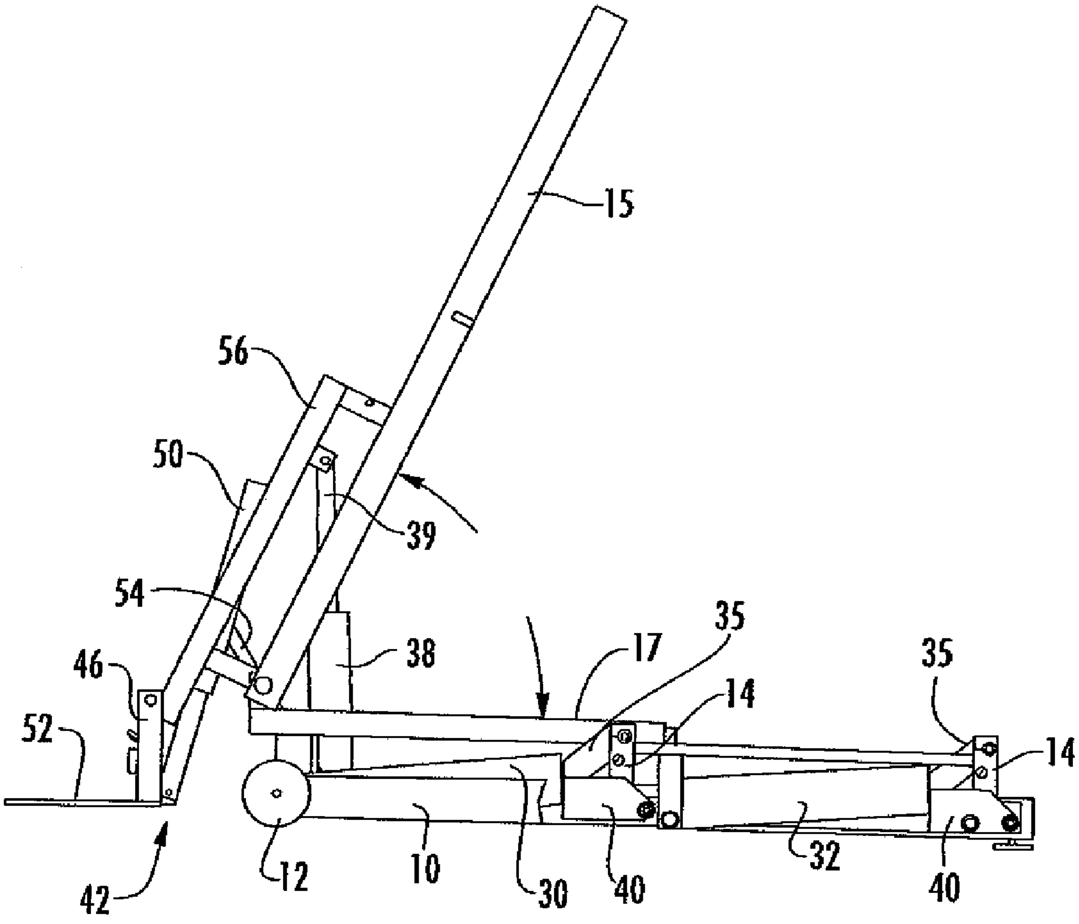
FIG. 4 is a side elevational view similar to FIGS. 2 and 3 but showing the table in a lowered horizontal position but in a fully tilted position.

Referring first to FIG. 1, the chiropractic table of the invention has a rectangular shaped base frame 10 that has a foot end 11 and a head end 13. If desired, a pair of rollers 12 may be provided at the end foot end 11 to facilitate movement of the table. The base frame 10 has two pair of upright supports 14 spaced apart on each side of the base frame 10 nearer the head end 13 that support the frame 10 on the floor. As best seen in FIGS. 2-5, the upper frame assembly 16 of the table has a sub-frame 17 and a patient support frame 15 pivotally connected at the foot end 11 of the table to the sub-frame 17. The support frame 15 supports separate sections for patient support including the head section 18, a chest section 20, a lumbar and pelvic section 22, and a footrest or ankle rest section 24. As is well known to those skilled in the art, the particular supports and mechanisms for independent movement of these sections vary depending upon the type of table, and they form no part of the invention. As illustrated in FIG. 1, each of the sections 18, 20, 22 and 24 are typically provided with cushions for the support and comfort of the patient. The cushions are shown only in FIG. 1 and have been eliminated from FIGS. 2-6 for the purposes of clarity in illustrating the mechanisms of the table that comprise the invention.

The sub frame 17 of the upper frame assembly 16 has arms 28 extending downwardly from its sides, and a cross bar 41 interconnects each opposing pair of arms 28. Parallel driver arms 30 and 32 have their upper ends pivotally connected to the cross bars 41, the driver arm 30 being connected to the cross bar 41 near the foot end 11 of the table while the driver arm 32 is connected to the cross bar 41 nearer the head end 13 of the table. Cross bars 41 connect each pair of arms 28 on the opposite sides of the table to provide strength and rigidity to the table. Cross bars 41 also allow the driver arms 30 and 32 to be positioned off the center of the table and thus open up the central area within the base frame 10. The driver arms 30 and 32 are connected at their lower ends within a linkage bar assembly 31 mounted inside the base frame 10. The linkage bar assembly 31 includes a longitudinally extending linkage bar 33 that interconnects the lower ends 40 of the driver arms 30 and 32 and to which the lower ends 40 are pivotally connected. Links 35 are pivotally connected to the upright supports 14 on one side of the frame 10, and the outer ends of each pair of links 35 are affixed to a cross member 37. Cross members 37 each extend from side to side and are affixed to the driver arms 30 and 32 between their pivot points. The foregoing described components form a moving parallelogram type linkage. To power the parallelogram linkage assembly, an elevating actuator 34 is mounted inside of the base frame 10 with its operating rod connected to the linkage bar 33. When activated, actuator 34 extends, extending the linkage bar 33 toward the foot end 11 of the table. Since the linkage bar 33 is connected to the driver arms 30 and 32, pushing the linkage bar 33 towards the foot end 11 of the table causes the driver arms 30 and 32 to elevate in a circular motion to elevate the upper frame assembly 16. When the actuator 34 is retracted, the driver arms 30 and 32 swing in the opposite directions to lower the upper frame assembly 16. Because of the positioning of the linkage assembly 31 and the driver arms closer to one side of the base frame 10, the open area in the center, free of cross supports, allows the upper frame assembly 16 to drop as low as possible thereby providing for lowering of the top of the table to a position in which the cushions are only about 18 inches or lower from the floor. This makes if much easier for the practitioner to conduct desired procedures, especially if he or she is short.

In order to make it easier for the patient to get off and on the table, the invention provides for tilting of the patient support frame 15 about the foot end 11 of the table. A tilt actuator or actuator 38 has its operating rod 39 pivotally connected to the patient support frame 15 with the actuator 38 being pivotally connected to the cross bar 41 that is nearer the foot end 11. This is the same pivot of the driver arm 30 to the cross bar 41. Tilt actuator 38 is operated simultaneously and synchronized with the elevating actuator 34 through hydraulic control valves 43 so that as the table is elevated, the support frame 15 will be tilted downwardly and as the table is lowered, the support frame 15 will be tilted upwardly to an angle of about 74 degrees from the horizontal. A hydraulic pump and motor 45 powers the hydraulic system. It should be understood that rather than hydraulic controls, electronic controls can be used to power the operations and to synchronize operation of the tilt actuator 38 and the elevating actuator 34. Providing for both elevation and tilting of the table by a single action of the practitioner saves the practitioner time and effort.

Figure 5:
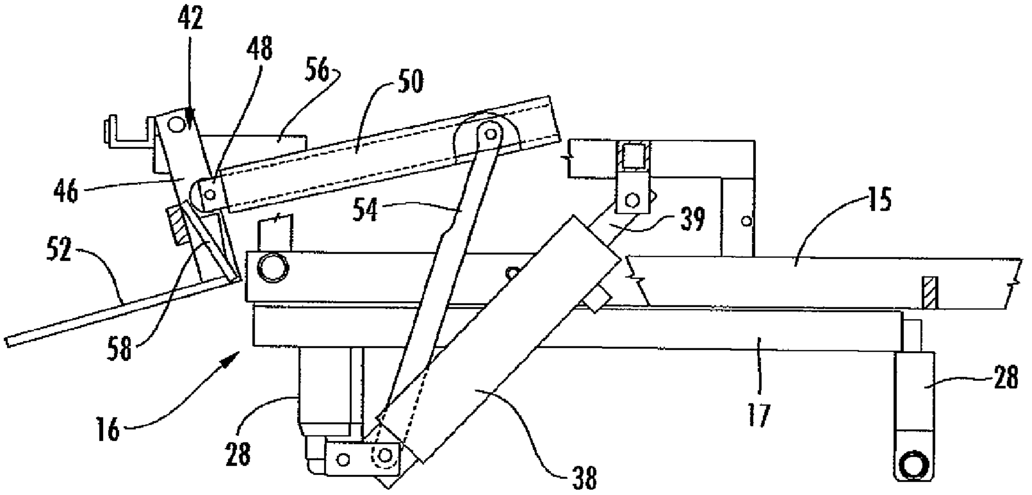
FIG. 5 is a side elevational view of a portion of the table with some components removed to better show the linkage and actuator assemblies for operating the footplate.
Figure 6:
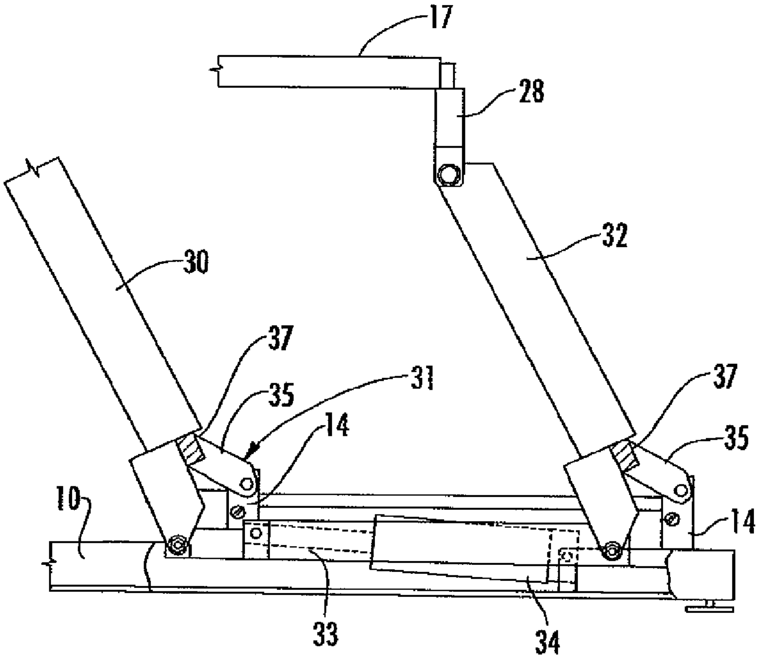
FIG. 6 is a side elevational view of a portion of the table with some components removed to better show the linkage for raising and lowering the table.

To make it easier for a patient to be properly positioned and feel more secure when getting on and off the table, a footplate assembly 42 is provided. Assembly 42 includes a foot plate 52 extending from a pair of arms 46 that are pivotally connected to the upper portion 56 of the patient support frame 15. A cam plate 58 is affixed to the arms 46 and a roller 48 is engageable with the cam plate 58 (FIG. 5). Roller 48 is mounted on the end of a linkage bar 50 that is pivotally connected to a link 54 which is pivotally connected to the cross bar 41 that extend from the sub frame 17. The footplate assembly 42 is operated by the tilt actuator 38 so that the foot plate 52 rotates to meet the patient's feet when the table is in the tilted position shown in FIG. 4 and rotates out of the way when the table is in the elevated position shown in FIG. 2. When the tilt actuator 38 is activated to tilt the table, the linkage bar 50 follows along with the actuator 38 to push the roller 48 against the cam plate 58 and rotate the footplate pad 52 up into position for the patient to step off the table when the table is tilted to the upright position shown in FIG. 4. When the table is tilted to this position, a patient can easily step onto the foot plate 52, grasp the table and be comfortably and securely held as the table is elevated and then tilted to the horizontal position shown in FIG. 2. As the table returns to the horizontal position, the footplate assembly 42 will cause the foot plate 52 to rotate downwardly out of the way of the practitioner.

From the foregoing description it will be evident that by a single action of the practitioner, the table will tilt and elevate and the footplate will be properly positioned. Having thus described the invention in connection with the preferred embodiments thereof, it will be evident to those skilled in the art that various revisions can be made to the preferred embodiments described herein without departing from the spirit and scope of the invention. It is my intention, however, that all such revisions will be included within the scope of the following claims.

What is claimed is:

1. A chiropractic table that will simultaneously tilt the table as it is lowered from an elevated position and also return the table to a horizontal position as it is elevated, said table comprising:

- a base frame providing a foot end and a head end for the table;
- an upper frame assembly having a foot end and a head end and having a sub-frame and a patient support frame pivotally connected to the sub-frame at the foot end;
- a linkage bar assembly combined with the base frame and having a movable linkage bar;
- a first driver arm having an upper end and a lower end with the upper end pivotally connected to the sub-frame near the foot end and the lower end pivotally connected to the base frame;
- a second driver arm having an upper end and a lower end with the upper end pivotally connected to the sub-frame near the head end and the lower end pivotally connected to base frame;
- the first and second driver arms being substantially parallel to each other with the linkage bar in the linkage assembly being pivotally connected to the driver arms beneath their lower end pivot connections with the base frame;
- a first power driven mechanism adapted to move the linkage bar forward and backward and thereby swing the driver arms to elevate and lower the sub-frame and the patient support frame;
- a second power driven mechanism pivotally connected between the sub-frame and the patient support frame to tilt the patient support frame from a substantially horizontal position to a more vertical position; and
- controls to synchronize the tilting of the patient support frame with the elevating and lowering of the sub-frame.

2. The chiropractic table of claim 1 in which the second power driven mechanism tilts the patient support frame to about 74° from the horizontal.

3. The chiropractic table of claim 1 in which the first power driven mechanism is a fluid cylinder pivotally connected to the base frame and having an operating rod connected to the linkage bar.

4. The chiropractic table of claim 1 in which the table is provided with:

- a footplate pivotally mounted to the patient support frame at the foot end; and
- a linkage assembly combined with the sub-frame and the footplate to cause the footplate to rotate upwardly when the patient support frame is tilted to a more vertical position thereby to provide a support for the patient to stand on, the linkage assembly also causing the footplate to rotate downwardly as the patient support frame moves to a more horizontal and elevated position.

5. The chiropractic table of claim 4 in which:

a pair of support arms extend laterally from the footplate, the support arms being pivotally connected to the patient support frame;

a cam plate is combined with the support arms; and a footplate linkage bar having a roller cam is pivotally connected to the sub-frame, the roller cam being engageable with the cam plate to cause the footplate to rotate as the patient support frame is tilted.

* * * * *